United States Patent
Blomquist

(10) Patent No.: US 7,210,476 B2
(45) Date of Patent: May 1, 2007

(54) BREATHING-SPEAKING VALVE

(76) Inventor: Inge Blomquist, Storgaten 26, S-567 32 Vaggeryd (SE)

( * ) Notice: Subject to any disclaimer, the term of this patent is extended or adjusted under 35 U.S.C. 154(b) by 70 days.

(21) Appl. No.: 10/672,835

(22) Filed: Sep. 18, 2003

(65) Prior Publication Data

US 2005/0072431 A1    Apr. 7, 2005

(30) Foreign Application Priority Data

Mar. 19, 2001 (SE) .................................... 0100953
Mar. 19, 2002 (WO) ...................... PCT/SE02/00523

(51) Int. Cl.
*A62B 18/08* (2006.01)

(52) U.S. Cl. ........................... 128/201.13; 128/201.25; 128/207.16

(58) Field of Classification Search ........... 128/207.16, 128/207.14, 205.27, 205.12, 201.19, 201.13, 128/200.26, 201.25, 205.28, 205.29, 206.17, 128/207.15

See application file for complete search history.

(56) References Cited

U.S. PATENT DOCUMENTS

| 4,538,607 | A | * | 9/1985 | Saul ....................... 128/207.16 |
| 4,763,645 | A | * | 8/1988 | Kapp ..................... 128/205.29 |
| 4,971,054 | A | * | 11/1990 | Andersson et al. ..... 128/207.16 |
| 5,765,557 | A | * | 6/1998 | Warters ................. 128/207.14 |

FOREIGN PATENT DOCUMENTS

WO   PCT/SE02/00523   2/2003

* cited by examiner

*Primary Examiner*—Justine R. Yu
*Assistant Examiner*—Shumaya Ali
(74) *Attorney, Agent, or Firm*—David I. Roche; Daniel A. Tallitsch; Baker & McKenzie LLP

(57) ABSTRACT

The present invention relates to a breathing-speaking valve intended to be used as a speaking valve of patients requiring filtration of inspiration air inhaled via tracheostomas and are mounted on a tracheal tube, which breathing-speaking valve includes a valve housing (1) inended to be attached to the tracheal tube and which comprises a check valve in the form of a membrane (10), which check valve opens when the patient inhales and closes at expiration and filter (7) for filtration of the inspiration air, which filter is located within this membrane, and optional, a nipple (6) for connection to a oxygen apparatus for oxygen delivery to the inspiration air whereby the filter (7) is laying against a number of ribs (5) located in the bottom (2) of the valve housing (1) and a nipple (6) for connection to a oxygen apparatus is mounted substantially perpendicular to the longitudinal direction of the valve housing (1) by the bottom of the valve housing (1), and said nipple (6) opens into the space (14) defined by the ribs (5) and the bottom (2) of the valve housing (1) and also opens into the filter (7) substantially parallel to the extension of the filter, whereby the distribution of the inspiration air and the optional oxygen delivery into the tracheal tube takes place in said space (14) and in the filter (7).

6 Claims, 1 Drawing Sheet

BREATHING-SPEAKING VALVE

THE TECHNICAL FIELD OF THE INVENTION

The present invention relates to a breathing valve intended to be used as a speaking valve for patients requiring filtration of inspiration air inhaled via tracheostomas and are mounted on a tracheal tube, which breathing-speaking valve includes a valve housing intended to be attached to the tracheal tube and which comprises a check valve in the form of a membrane, which opens the patient inhales and closes when the patient exhales, and a filter for filtration of the inspirator air, which filter is located within this membrane.

DESCRIPTION OF THE BACKGROUND ART

Different types of solutions for breathing valves including membranes are known to the above-mentioned art to make the valve useful as a speaking valve. The valves are large and clumsy and therefore difficult for the user to hide behind e.g. collars, scarves, etc., and the valves often have difficulties to distribute the air evenly through the filter. As an example, patent SE B 462 367 may be mentioned. Said patent discloses a breathing valve intended to be used as a speaking valve having a nipple for connection to an oxygen apparatus. This breathing valve is awkward under certain circumstances and has the disadvantage that it does not always evenly distribute and mix the inspiration air with oxygen when inspiring; the filter can disturb the delivery of oxygen, as the nipple for oxygen is situated behind the filter and the filter is easily pressed down against the bottom of the valve housing in the inspiration step.

Further, the respiratory passages are very often dried up when breathing only through the valve. The expiration air can not damp the filter of the valve when breathing through natural respiratory passages and one is able to speak.

BRIEF DISCLOSURE OF THE INVENTIVE CONCEPT

An object of the present invention is to eliminate the above mentioned drawbacks of breathing valves and to provide a breathing valve evenly distributing the inspiration air and optional oxygen delivery by the filter and enabling external damp to be supplied to the valve and thereby preventing drying up of the respiratory passages.

According to the inventive concept, the above mentioned problem is solved by placing the filter against a number of ribs located in the bottom of the valve housing and a nipple for connection to an oxygen apparatus for oxygen delivery to the inspiration air and mounted substantially perpendicular to the longitudinal direction of the valve housing by the bottom of the valve housing, and said nipple opens into the space defined by the ribs and the bottom of the valve housing and also opens into the filter parallel to the extension of the filter, whereby the distribution of the inspiration air and the optional oxygen delivery into the tracheal tube takes place in said space and in the filter.

According to the inventive concept additionally a breathing valve is obtained which is reliable and durable, humidifying the inspiration air, easy to clean, small and handy and gives the user a higher quality of life as it can be easily hidden underneath a collar, a shawl or the like.

DETAILED DESCRIPTION OF A PREFERRED EMBODIMENT OF THE INVENTION

Figure 1:
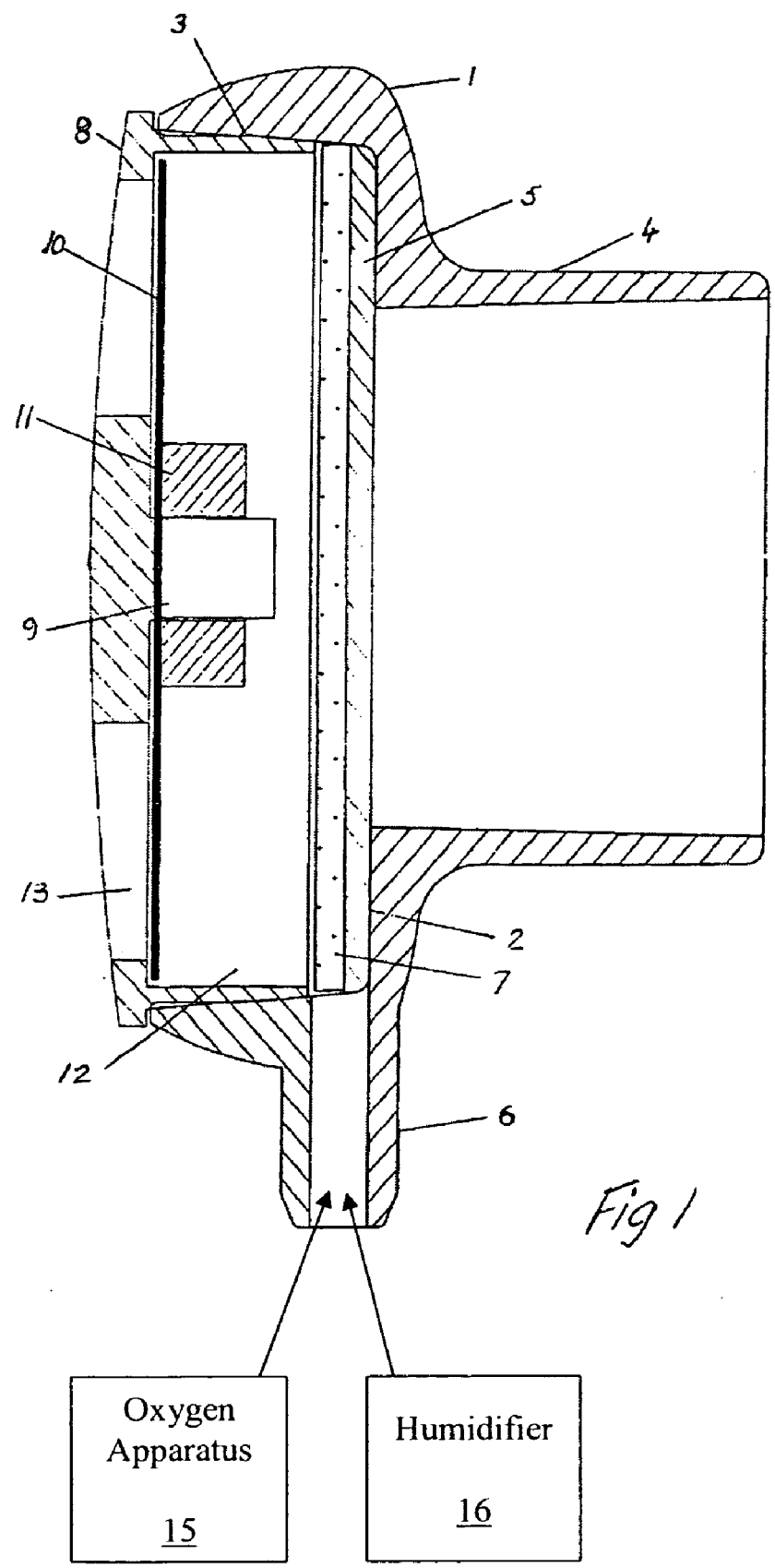
FIG. 1 is a sectioned side view of a breathing valve according to the invention.

FIG. 1 shows the valve housing 1 of the breathing valve according to the invention with bottom 2, walls 3, a tubular stub 4 connectable to a tracheal tube, a number of ribs 5 in the bottom 2 of the valve housing, and a nipple 6 for oxygen delivery from an oxygen apparatus 15. The stud has tapered design to fit common tracheal tubes.

From FIG. 1 it is clear how a filter 7 is arranged in the bottom 2 of the valve housing 1, right in front of a nipple 6 for oxygen delivery, and on the ribs 5 which is extending from the center valve housing 1 and radiate to its periphery. The diameter of the nipple 6 is between 1.5 and 5.5 mm. The height of the ribs 5 are between 0.5 and 3.0 mm thick, preferably 1 mm. A cap 8 with a center neck 9 for fastening of a membrance 10 and a membrance holder 11 is arragned over this membrane 10 over the opening 12 of the valve housing 1. The cap 8 has a number of openings 13 through which the inspiration air flows and will easily open the membrane 10 which is a thin, ductile and silent working silicone membrane 10. When exhaling, the membrane 10 is closing the valve and the exhaling is done through the natural respiratory passages and thus the user is able to speak in a common way. The filter 7 of the valve is whole or partly made of e.g. electrostatic polymer filter which is a very thin material, about 1.5 mm, preferably 2 mm thick, and which is cleaning the inspiration air on a particular effective way of particles with a size of 0.3–1.0 micron and which filter is silent during use. The filter can also wholly or party be made of a convention filter of cell plastic, paper, fibre material or the same. The valve housing 1 and the cap 8 have arched areas and have a total length of the breathing valve of about 22 mm, of which length only 10 mm extends out from the tracheal tube.

When the air, which exhales via the valve, is dry due to the fact that it is not humidified by the mucous membrane, it is suitably with a humidifier 16 which e.g. is able to be connected to an opening in the oxygen nipple or to an opening, channel or the like in the bottom of the valve housing or in the walls or in any other way to supply damp to the filter and in this way be able to increase and/or regulate the humidity of the inspiration air. The filter is acting as the mucous membrane in e.g. the nose, which humidifies the inhaled air when inhaling through the nose. If somebody is inhaling and exhaling through a valve where the membrane is taken away, the valve is acting as an air humidifier and can advantage be used also in the night. The filter is absorbing moisture from the expiration air and leave it to the inspiration air and counteracts in this way drying up the bronchial tubes. Even here a moisture of the inhaled air is suitable, e.g. through a special prepared filter to give extra moisture to the inspiration air.

By night, the valve can also be used only as a breathing valve with a humidifier by taking the membrane away, or it can also be delivered without a membrane and only be used as a humidifier.

Breathing-speaking valve can also be mounted on the tracheal tube by the fact that the tubular stud has a shorter longitudinal direction and can be shaped as a bayonet socket, quick coupling of any suitable kind or the same to simplify the arrangement on the tracheal tube and to shorten the longitudinal direction of the valve.

It is also possible to make the valve in one piece with a hose, an inner cannula (tube), which is moved into an outer tracheal tube, and is mounted at this tracheal tube instead of a tubular stud which is mounted at a tracheal tube.

The filter, the membrane, the cap and the valve housing can easily be replaced and be cleaned as required.

It will be noted that the invention naturally can be modified in many ways within the scope of the appended claims.

The invention claimed:

1. A breathing-speaking valve intended to be used as a speaking valve for patients requiring filtration of inspiration air inhaled via tracheostomas mounted on a trachea tube, which breathing-speaking valve includes a valve housing intended to be attached, via its bottom, to the trachea tube and which comprises a check valve in the form of a membrane, which check valve opens when the patient inhales and closes when the patient exhales and a filter for filtration of the inspiration air, which filter is located between said membrane and the bottom of the housing, characterized in that the filter is laying against a number of ribs located in the bottom of the valve housing and a nipple for connection to an oxygen apparatus for oxygen delivery to the inspiration air and mounted substantially perpendicular to a longitudinal direction of the valve housing by the bottom of the valve housing, and said nipple opens into a space defined by the ribs and the bottom of the valve housing and also opens into the filter parallel to the extension of the filter, whereby the distribution of the inspiration air and the optional oxygen delivery into the trachea tube takes place in said space and in the filter.

2. Breathing valve according to claim 1, characterized in that an external humidifier is mounted to deliver humidity to the filter.

3. Breathing valve according to claim 2, characterized in that the humidifier is connected to the oxygen nipple or to a special nipple on this oxygen nipple.

4. Breathing valve according to claim 1, characterized in that the thickness of the filter is between 0.5 and 3.0 mm, preferably 2 mm.

5. Breathing valve according to claim 1, characterized in that height of the ribs are between 0.5 and 3.0 mm, preferably 1 mm.

6. Breathing valve according to claim 1, characterized in that the nipple for oxygen delivery have a diameter between 1.5 and 5.5 mm.

* * * * *